US 6,983,651 B2

(12) United States Patent
Bandou

(10) Patent No.: US 6,983,651 B2
(45) Date of Patent: Jan. 10, 2006

(54) TIRE EARTH EFFECT CHECKING METHOD AND APPARATUS

(75) Inventor: Eiji Bandou, Hiratsuka (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 3 days.

(21) Appl. No.: 10/853,105

(22) Filed: May 26, 2004

(65) Prior Publication Data

US 2004/0237639 A1    Dec. 2, 2004

(30) Foreign Application Priority Data

Jun. 2, 2003   (JP)   ............................. 2003-156354

(51) Int. Cl.
*G01M 17/02*    (2006.01)
(52) U.S. Cl. ....................................................... 73/146
(58) Field of Classification Search .................. 73/146; 156/136, 137, 349; 209/509, 520
See application file for complete search history.

(56) References Cited

U.S. PATENT DOCUMENTS 6,536,597 B1 *   3/2003   Farne et al. ................. 209/520
6,802,212 B2 *  10/2004   Farne .......................... 73/146

FOREIGN PATENT DOCUMENTS

JP    2002-337246 A1    11/2002

* cited by examiner

*Primary Examiner*—David Gray
*Assistant Examiner*—George P. Bonanto
(74) *Attorney, Agent, or Firm*—Rader, Fishman & Grauer PLLC

(57) ABSTRACT

Ions are imparted to a tire by ion generating means to electrically charge the tire. Then, the electrically charged tire is electrically connected to an earth by earth means to discharge electric charges therefrom. Thereafter, an electrification voltage of the tire from which electric charges have been discharged is detected by electrification voltage detection means.

12 Claims, 3 Drawing Sheets

TIRE EARTH EFFECT CHECKING METHOD AND APPARATUS

BACKGROUND OF THE INVENTION

The present invention relates to a method and apparatus for checking an earth effect of a tire and, more particularly, to a tire earth effect checking method and apparatus which can highly reliably check the earth effect of a tire.

In recent years, in order to improve fuel consumption and drainage performance by lowering rolling resistance, rubber mixed with a large amount of silica has been used for the rubber portion of the tread of a pneumatic tire. With an increase in the amount of silica, the amount of carbon decreases to thereby lower electrical conductivity with respect to a road surface. As a result, the vehicles keep static electricity, which can badly affect noise interference with a radio and the like, and vehicle fire.

To eliminate static electricity from the vehicle, there are proposed a lot of tires in which the rubber portion of the tread consists of a cap tread rubber layer mixed with a large amount of silica, and a under tread rubber layer, disposed inwardly thereof, mixed with a large amount of carbon, and an earth rubber part for connecting the under tread rubber layer and a road surface is provided in the cap tread rubber layer so that the earth rubber part is exposed on the surface of the cap tread rubber layer. The static electricity is discharged from the vehicle through the earth rubber part to a road surface.

In order to check the effect of the earth rubber part of such tires, there is disclosed a technology in Published Unexamined Japanese Patent Application No. 2002-337246, which measures an electric resistance value of the tire by applying a voltage between the rim of a wheel on which the tire is mounted, and the tread surface on which the earth rubber part exposes. The electrical conductivity of the tire (the earth effect of the earth rubber part) is judged on the basis of the electric resistance value.

However, the above technology requires a troublesome operation of assembling the tire to the rim of a wheel, and the contact state of an electrode which is electrically connected to the tread surface varies due to patterns of the tread surface. Therefore, there is variation in the electric resistance value obtained, and a problem arises such as a decrease in reliability of the earth effect.

SUMMARY OF THE INVENTION

It is an object of the present invention to provide a tire earth effect checking method and apparatus which require no operation of assembling a tire to the rim of a wheel and can highly reliably check the earth effect of a tire.

To achieve the above object, a tire earth effect checking method according to the present invention comprises the steps of:

imparting ions to a tire to electrically charge the tire;

electrically connecting the electrically charged tire to an earth to discharge electric charges therefrom; and detecting an electrification voltage of the tire form which electric charges have been discharged.

A tire earth effect checking apparatus according to the present invention comprises:

ion generating means for imparting ions to a tire to electrically charge the tire;

earth means for electrically connecting the electrically charged tire to an earth; and electrification voltage detection means for detecting an electrification voltage of the earthed tire.

Another tire earth effect checking apparatus according to the present invention is a tire earth effect checking apparatus for checking an earth effect of a tire which is conveyed to an inspection process by a conveyor after curing, comprising:

centering means for centering the tire on the conveyor;

ion generating means for imparting ions to the centered tire to electrically charge the centered tire;

earth means for electrically connecting a tread of the electrically charged tire to an earth; and electrification voltage detection means for detecting an electrification voltage of the earthed tire.

In accordance with the present invention, ions are imparted to electrically charge a tire, the electrically charged tire is grounded to discharge electric charges therefrom, and then an electrification voltage of the grounded tire is detected. Therefore, a troublesome operation of assembling a tire to the rim of a wheel is not necessary, while the electrification voltage of the tire can be detected in a state which is very near to a practical situation to thereby allow an earth effect of the tire to be highly reliably and easily checked.

DETAILED DESCRIPTION OF THE PREFERRED EMBODIMENTS

The embodiments of the present invention will be described in detail with reference to the attached drawings.

Figure 1:
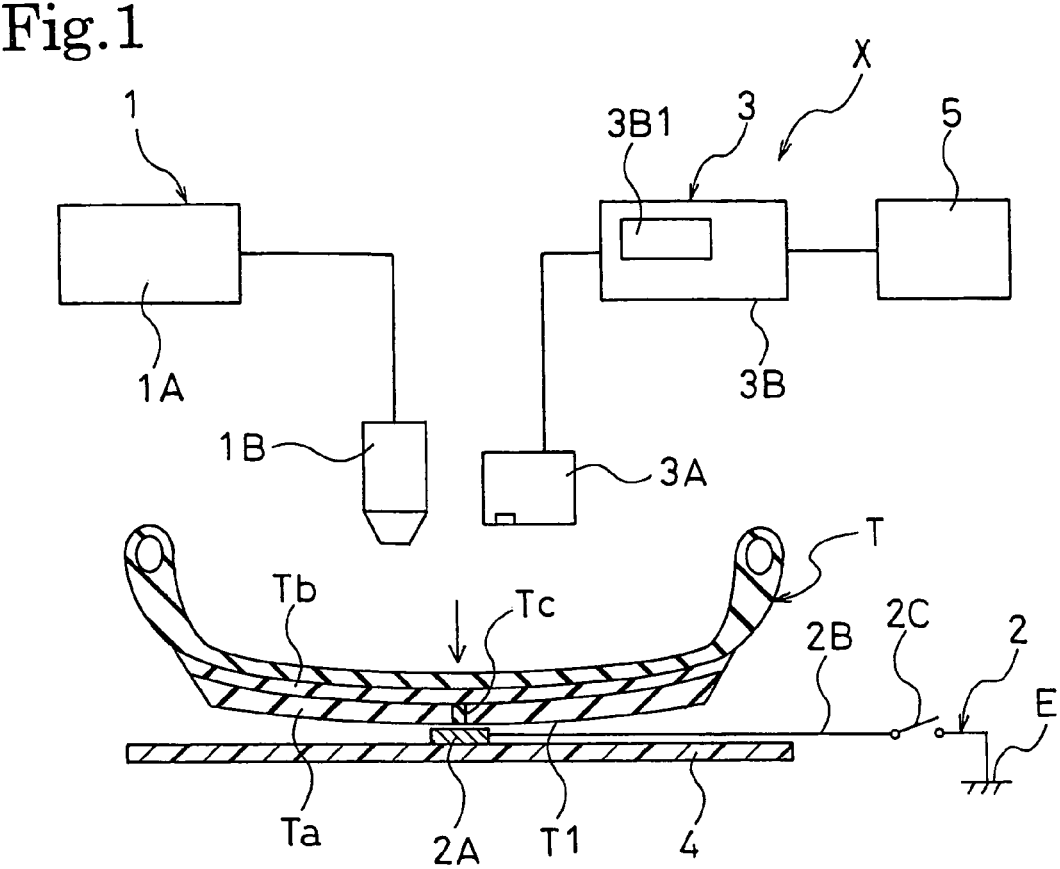
FIG. 1 is an explanatory drawing showing an embodiment of a tire earth effect checking apparatus according to the present invention.

Referring to FIG. 1, reference character X denotes a tire earth effect checking apparatus according to the present invention, reference numeral 1 denotes ion generating means for imparting ions to a tire T to electrically charge the tire T, reference numeral 2 denotes earth means for earthing the electrically charged tire T, and reference numeral 3 denotes electrification voltage detection means for detecting an electrification voltage of the earthed tire T. The tire T includes a tread Ti having a cap tread rubber layer Ta mixed with a large amount of silica, and a under tread rubber layer Tb mixed with a large amount of carbon. An earth rubber part Tc mixed with a large amount of carbon to have a high electrical conductivity is annularly provided in the cap tread rubber layer Ta along the center of the tread T1.

The ion generating means 1 comprises an ion generating unit 1A and an ion applying head 1B connected to the ion generating unit 1A. Positive ions are generated in the ion generating unit 1A, and are applied to the tire T by the ion applying head 1B to electrically charge the tire T.

The ion generating unit 1A may be structured to generate negative ions in place of positive ions. Alternatively, the ion generating unit 1A may be structured such that the ion generating unit 1A can generate positive and negative ions, and the amount of generation of positive and negative ions is adjustable. The ion generating unit generates positive and negative ions containing either of them more than the other, which are applied to the tire T by the ion applying head 1B. The ion generating unit 1A may have any structure which can electrically charge the tire T with ions.

The earth means 2 includes an electrode 2A placed on an insulator 4 formed from an acrylic plastic plate or the like, and an earth connection wire 2B for electrically connecting between the electrode 2A and earth E. The tire T can be electrically connected to the earth E through the electrode 2A and earth connection wire 2B. The earth connection wire 2B has a switch 2C, and when the switch 2C is on, the electrode 2A is electrically connected to the earth E, and when the switch 2C is off, the electrical connection between the electrode 2A and the earth E is cut off.

The electrification voltage detection means 3 includes a non-contact type detection head 3A for detecting an electrification voltage of the tire T, and a processing unit 3B electrically connected to the detection head 3A. The processing unit 3B is arranged such that the processing unit 3B processes signals of the electrification voltage of the tire T detected by the detection head 3A and the electrification voltage values are digitally indicated on the display section 3B1 of the processing unit 3B.

The processing unit 3B is electrically connected to recording means 5, which records data of electrification voltage of the tire T in time-series.

Figure 2:
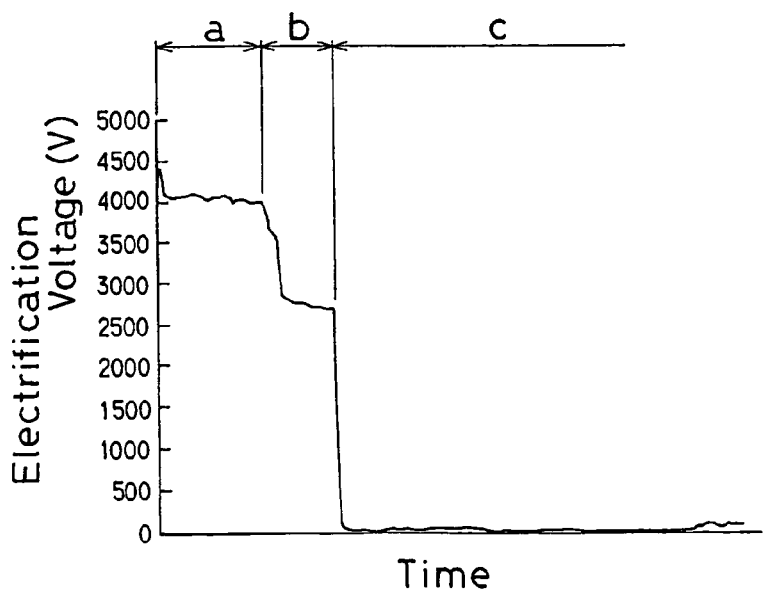
FIG. 2 is a graph showing one example of the electrification voltage variation of an electrically charged test tire piece in time-series, detected by the electrification voltage detection means.

A tire earth effect checking method according to the present invention will be described below with reference to FIG. 2, using the tire earth effect checking apparatus X mentioned above. FIG. 2 shows a time-series voltage variation of an electrically charged test piece into which the tire T is cut in cross section shown in FIG. 1.

First, the electrification voltage detection means 3 is turned on, and the ion generating unit 1A then generates positive ions. The positive ions are applied to the tire T through the ion applying head 1B to thereby electrically charge the tire T. A predetermined amount of positive ions are imparted to electrically charge the tire T with a predetermined amount of positive charges, and the electrically charged tire T is then left for a predetermined period of time (for example, about five seconds) as it is until the electrification voltage detected by the electrification voltage detection means 3 is in a substantially even level where the variation thereof is within a certain range (see a first area a in FIG. 2). A predetermined amount of positive ions may be imparted so that the electrification voltage of the electrically charged tire T is 3 kV or more, and the electrification voltage of about 4.4 kV is exemplified in FIG. 2.

In turn, an area in which the earth rubber part Tc of the tread T1 is positioned is press contacted to the electrode 2A, and this state is kept for a predetermined period of time (for example, about three seconds) until the electrification voltage is in a substantially even level as described above (see a second area b in FIG. 2). Thereafter, the switch 2C is turned on to electrically connect the earth means 2 to the earth E, whereby electric charges are discharged from the electrically charged tire T (see a third area c in FIG. 2).

According to the tire T having the earth rubber part Tc shown in FIG. 1, the electric charges are discharged from the tire T to the earth E through the earth rubber part Tc, electrode 2A and earth connection wire 2B, and therefore, low electrification voltages shown in FIG. 2 are detected by the electrification voltage detection means 3. This electrification state shows that the tire T has a high earth effect. Data of the electrification voltages of the tire T detected from the beginning of operation of the electrification voltage detection means 3 is sequentially recorded by the recording means 5.

Figure 3:
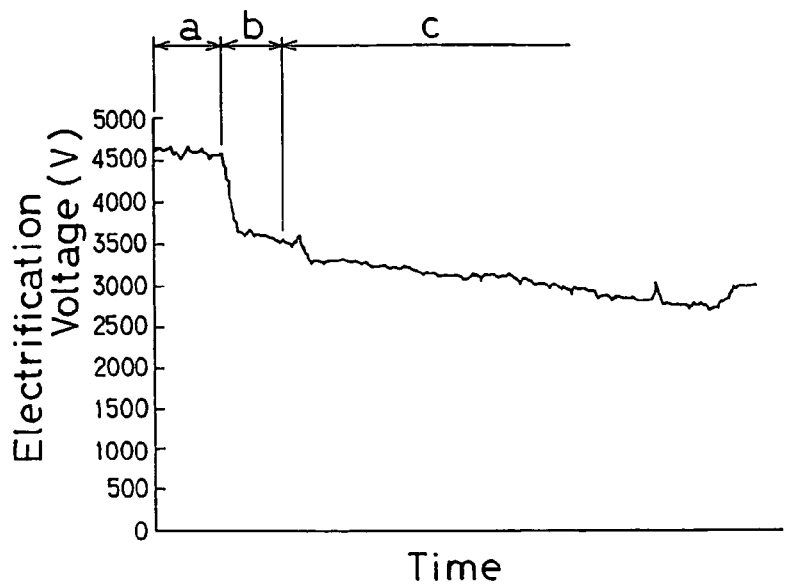
FIG. 3 is a graph showing another example of the electrification voltage variation of an electrically charged test tire piece in time-series, detected by the electrification voltage detection means.

FIG. 3 shows a time-series electrification voltage variation of an electrically charged test piece of a tire with no earth rubber part. The electrification voltages of the tire without the earth rubber part Tc detected after discharging are high, and this electrification state shows that the tire has a low earth effect.

As described above, according to the present invention, ions are imparted to electrically charge the tire T, the electrically charged tire T is grounded, and then the electrification voltages of the grounded tire T are detected. Therefore, a troublesome operation of assembling the tire to the rim of a wheel is not necessary, and by electrically charging the tire T with ions, the electrification voltages of the tire T can be detected in a state which is very near to a practical situation, thereby allowing the tire earth effect to be highly reliably and easily checked.

The time-series detection of electrification voltages of the tire T from the beginning to the end by the electrification voltage detection means 3 provides electrification voltage data as shown in FIGS. 2 and 3, thus allowing an earth characteristic of the tire T to be easily evaluated using the data.

Figure 4:
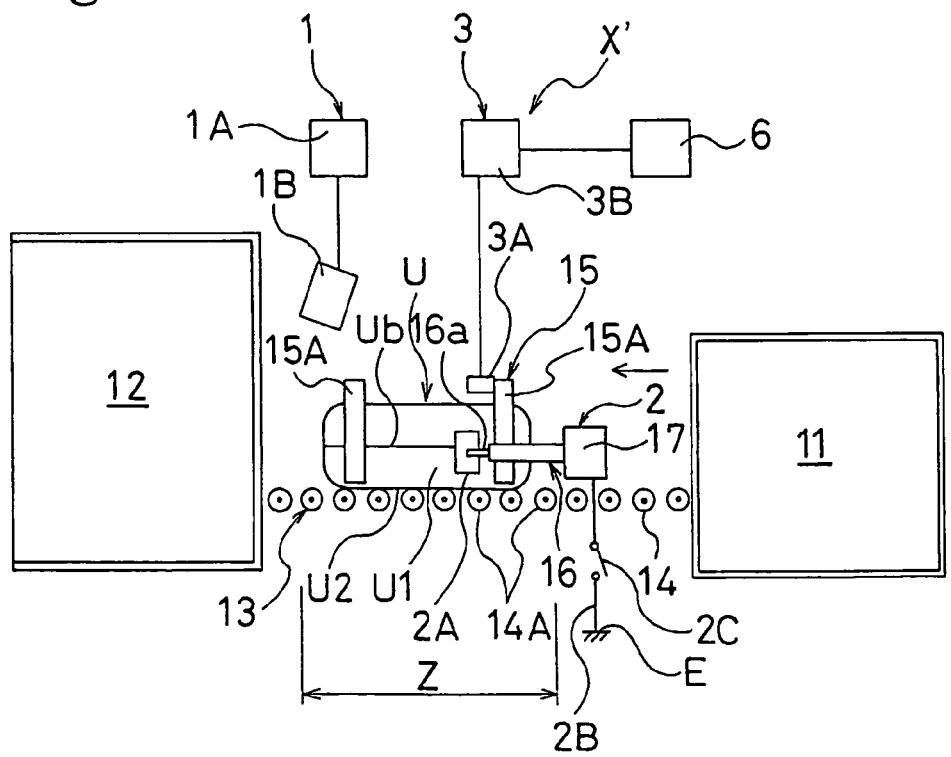
FIG. 4 is a front explanatory drawing showing another embodiment of a tire earth effect checking apparatus according to the present invention.
Figure 5:
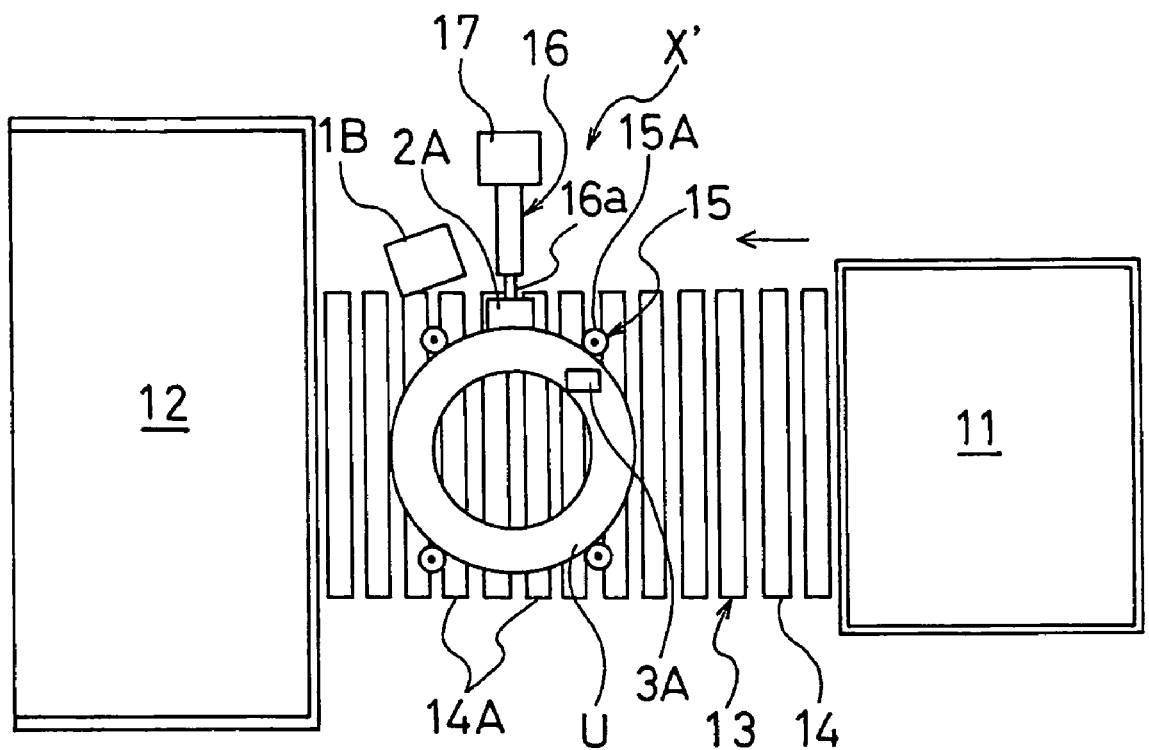
FIG. 5 is a top explanatory drawing of FIG. 4.

FIGS. 4 and 5 show another embodiment of a tire earth effect checking apparatus according to the present invention, which is incorporated into a tire manufacturing line. Reference character U denotes a tire after curing, reference character U1 denotes a tread of the tire U, reference character U2 denotes a sidewall of the tire U, and reference character Ub denotes an earth rubber part annularly exposing along the center of the tread U1. Reference numeral 11 denotes a tire press, reference numeral 12 denotes an inspection device for inspecting, for example, uniformity of the tire U which has been cured in the tire press 11, and reference numeral 13 denotes a roller conveyor for conveying the tire U from the tire press 11 to the inspection device 12.

The tire earth effect checking apparatus X' is installed between the tire press 11 and the inspection device 12, and checks up an earth effect of the tire U conveyed by the roller conveyor 13 to the inspection process after curing.

The roller conveyor 13 includes a plurality of rotatable rollers 14 which are horizontally aligned, and a detection area Z for detecting an electrification voltage of the tire U which has been electrically charged. Rollers 14A of the plurality of rollers 14 located in the detection area Z are covered with an insulation material to electrically insulate the rollers 14A from the tire U, thereby preventing electric charges from being discharged from the sidewall U2 to the rollers 14A when the tire U is electrically charged. In place of the roller conveyor 13, a belt conveyor may be used. In case of using a belt conveyor, if the conveyor belt is formed of rubber with high electrical insulation property, the surface thereof which comes into contact with the tire U does not need to be electrically insulated.

Provided in the detection area Z in which the rollers 14A are disposed is tire centering means 15 for centering the tire U. The tire centering means 15 includes four vertically extending centering roads 15A, which are placed above the rollers 14A in predetermined intervals and are movable in synchronization with each other in a width direction of the roller conveyor 13, and the tire U which has reached the detection area Z can be centered by the centering roads 15A.

In the above tire earth effect measuring apparatus X' incorporated into the tire manufacturing line, the electrode 2A of the earth means 2 is fixedly attached to the tip of the metal road 16a of a metal cylinder actuator 16. The cylinder actuator 16 is supported by a metal holder 17, and the earth connection wire 2B electrically connects between the metal holder 17 and the earth E. The electrode 2A is press contacted to the tread U1 by extending the metal road 16a, whereby the tire U is grounded to the earth E through the electrode 2A, metal cylinder actuator 16, metal holder 16, and earth connection wire 2B.

Determination means 6 for determining an earth effect of the tire U is electrically connected to the processing unit 3B of the electrification voltage detection means 3 in place of the recording means 5, and an earth examination of the tire U after curing can be carried out by the determination means 6.

The determination means 6 determines as follows. Data of electrification voltage, after discharging, of the electrically charged tire U input from the processing unit 3B, and the pre-set reference voltage value (for example, 0.5 kV) are compared, and if the electrification voltage data after discharging are equal to or lower than the reference voltage value, the determination means 6 determines that the earth effect is good, and if the electrification voltage data after discharging are higher than the reference voltage value, the determination means 6 determines that the earth effect is bad.

According to the tire earth effect checking apparatus X' shown in FIGS. 4 and 5, the tire U which has reached the detection area Z is centered by the centering means 15, and the electrode 2A is then press contacted to an area where the earth rubber part Ub of the tread U1 is located. The switch 2C of the earth means 2 is off at this time, and the circuit of the earth means 2 is open. Then, the ion generating unit 1A generates positive ions, and the positive ions are applied to the tire U through the ion applying head 1B. A predetermined amount of positive ions are imparted to electrically charge the tire U with a predetermined amount of positive charges.

The electrically charged tire U is left for a predetermined period of time (for example, about three seconds) as it is until the electrification voltage of the electrically charged tire U is in a substantially even level, and the switch 2C of the earth means 2 is turned on to close the circuit thereof to thereby discharge electric charges from the electrically charged tire U to the earth E. Thereafter, the electrification voltage detection means 3 is turned on to detect an electrification voltage of the tire U from which electric charges has been discharged. The determination means 6 determines whether the tire U has a good earth effect or does not, base on the data of the detected electrification voltage.

As described above, according to the tire earth effect checking apparatus X' incorporated into a tire manufacturing line, in addition to the above effects that no operation of assembling the tire to the rim of a wheel is required and the earth effect of the tire U can be highly reliably and easily checked, a time consuming troublesome operation such as an operation of assembling a tire to the rim of a wheel is not required, whereby whether the earth effect of the tire U is good or not can be determined while one tire is inspected by the inspection device 12. Thus, an earth property examination can be carried out without suffering deterioration of an inspection process in the inspection device 12.

The preferred embodiments of the present invention have been described above. However, the present invention may be embodied in other specific forms without departing from the spirit or essential characteristics thereof. The present embodiments are therefore to be considered in all respects as illustrative and not restrictive, the scope of the present invention being indicated by the appended claims rather than by the foregoing description and all changes which come within the meaning and range of equivalency of the claims are therefore intended to be embrace therein.

What is claimed is:

1. A tire earth effect checking method comprising the steps of:
    imparting ions to a tire to electrically charge the tire;
    electrically connecting the electrically charged tire to an earth to discharge electric charges therefrom; and
    detecting an electrification voltage of the tire from which electric charges have been discharged.

2. A tire earth effect checking method according to claim 1, wherein the step of electrically connecting the electrically charged tire comprises electrically connecting a tread of the electrically charged tire to an earth.

3. A tire earth effect checking method according to claim 1, wherein the step of imparting ions comprises imparting a predetermined amount of ions to a tire to electrically charge the tire, and the step of electrically connecting the electrically charged tire to an earth is performed after finishing the ion imparting step.

4. A tire earth effect checking method according to claim 1, further comprising the step of determining whether an earth effect of the tire is above a predetermined level, based on the detected electrification voltage.

5. A tire earth effect checking method according to claim 1, wherein the ions are positive ions or negative ions.

6. A tire earth effect checking apparatus comprising: ion generating means for imparting ions to a tire to electrically charge the tire; earth means for electrically connecting the electrically charged tire to an earth; and electrification voltage detection means for detecting an electrification voltage of the earthed tire.

7. A tire earth effect checking apparatus according to claim 6, further comprising determination means for determining whether an earth effect of the tire is above a predetermined level, based on the detected electrification voltage, the determination means being electrically connected to the electrification voltage detection means.

8. A tire earth effect checking apparatus according to claim 6, wherein the ions are positive ions or negative ions.

9. A tire earth effect checking apparatus for checking an earth effect of a tire which is conveyed to an inspection process by a conveyor after curing, comprising:
    centering means for centering the tire on the conveyor;
    ion generating means for imparting ions to the centered tire to electrically charge the centered tire;
    earth means for electrically connecting a tread of the electrically charged tire to an earth; and
    electrification voltage detection means for detecting an electrification voltage of the earthed tire.

10. A tire earth effect checking apparatus according to claim 9, wherein the conveyor has a detection area and comprises a roller conveyor having a plurality of rollers, the rollers positioned in the detection area being structured to be electrically insulated from the tire.

11. A tire earth effect checking apparatus according to claim 9, further comprising determination means for determining whether an earth effect of the tire is above a predetermined level, based on the detected electrification voltage, the determination means being electrically connected to the electrification voltage detection means.

12. A tire earth effect checking apparatus according to claim 9, wherein the ions are positive ions or negative ions.

* * * * *